US007211582B1

(12) United States Patent
Aberg et al.

(10) Patent No.: US 7,211,582 B1
(45) Date of Patent: May 1, 2007

(54) METHODS FOR TREATING URTICARIA USING DESCARBOETHOXYLORATADINE

(75) Inventors: A. K. Gunnar Aberg, Westborough, MA (US); John R. McCullough, Worcester, MA (US); Emil R. Smith, Shrewsbury, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 09/447,218

(22) Filed: Nov. 23, 1999

Related U.S. Application Data

(62) Division of application No. 09/039,260, filed on Mar. 16, 1998, which is a division of application No. 08/783,393, filed on Jan. 13, 1997, now Pat. No. 5,731,319, which is a division of application No. 08/366,651, filed on Dec. 30, 1994, now Pat. No. 5,595,997.

(51) Int. Cl.
*A61K 31/44* (2006.01)
(52) U.S. Cl. .................................. 514/290; 546/93
(58) Field of Classification Search ............. 514/290, 514/291, 292, 826; 546/93
See application file for complete search history.

(56) References Cited

U.S. PATENT DOCUMENTS

| | | | | |
|---|---|---|---|---|
| 3,326,924 A | * | 6/1967 | Villani .......................... | 546/93 |
| 3,391,143 A | * | 7/1968 | Kaiser et al. ................ | 546/103 |
| 3,536,809 A | | 10/1970 | Applezweig ................. | 424/28 |
| 3,598,123 A | | 8/1971 | Zaffaroni .................... | 128/268 |
| 3,940,485 A | | 2/1976 | Levinson et al. ........... | 424/250 |
| 4,282,233 A | * | 8/1981 | Vilani ......................... | 514/290 |
| 4,371,516 A | | 2/1983 | Gregory et al. ............. | 424/485 |
| 4,659,716 A | | 4/1987 | Villani et al. ............... | 514/290 |
| 4,777,170 A | | 10/1988 | Heinrich ................... | 514/226.2 |
| 4,990,535 A | | 2/1991 | Cho et al. ................... | 514/556 |
| 5,019,591 A | | 5/1991 | Gardner et al. ............ | 514/253 |
| 5,089,496 A | | 2/1992 | Piwinski et al. ........... | 514/253 |
| 5,100,675 A | | 3/1992 | Cho et al. ................... | 424/468 |
| 5,314,697 A | | 5/1994 | Kwan et al. ................ | 424/480 |
| 5,595,997 A | * | 1/1997 | Aberg et al. ................ | 514/290 |
| 5,714,501 A | | 2/1998 | Timmerman et al. ....... | 514/325 |
| 5,731,319 A | * | 3/1998 | Aberg et al. ................ | 514/290 |
| 5,900,421 A | | 5/1999 | Handley et al. ............ | 514/290 |

FOREIGN PATENT DOCUMENTS

| | | |
|---|---|---|
| EP | 0 288 640 | 11/1988 |
| EP | 396404 | 11/1990 |
| EP | 0780127 | 6/1997 |
| WO | W O 85/03707 A1 | 8/1985 |
| WO | WO 85/03707 | 8/1985 |
| WO | WO85/03707 A1 * | 8/1985 |
| WO | WO 92/00293 | 1/1992 |
| WO | WO 92/11034 | 7/1992 |
| WO | WO 92/20377 | 11/1992 |
| WO | WO 96/20708 | 7/1996 |
| WO | WO 97/28797 | 8/1997 |
| WO | WO 99/32125 | 7/1999 |

OTHER PUBLICATIONS

Berkow et al. (eds.), *The Merck Manual of Diagnosis and Therapy*, 16th Edition, Merck Research Laboratories, Rahway, NJ, May 1992, only pp. 332-334 supplied.*
Gennaro et al. (eds.), *Remington's Pharmaceutical Sciences, 18th Edition*, Mack Publishing Co., Easton, PA, 1990, only pp. 678 and 1123-1124 (from Chs. 34 & 59, respectively) are supplied.*
Thomas et al. (eds.), *Taber's Cyclopedic Medical Dictionary, 17th Illustrated Edition*, F. A. Davis Company, Philadelphia, PA, 1993, only pp. 2091-2092 supplied.*
Berkow et al. (eds.), *The Merck Manual of Diagnosis and Therapy*, 16th Edition, Merck Research Laboratories, Rahway, NJ, May 1992, only pp. 332-334 supplied.*
Gennaro et al. (eds.), *Remington's Pharmaceutical Sciences, 18th Edition*, Mack Publishing Co., Easton, PA, 1990, only pp. 678 and 1123-1124 (from Chs. 34 & 59, respectively) are supplied.*
Thomas et al. (eds.), *Taber's Cyclopedic Medical Dictionary, 17th Illustrated Edition*, F. A. Davis Company, Philadelphia, PA, 1993, only pp. 2091-2092 supplied.*
Bocian, R, "Hay Fever (Allergic Rhinitis): Current Management Approaches," Palo Alto Medical Foundation, Spring, 2000, see <http://www.pamf.org/health/toyourhealth/hayfever/html>.*
E. W. Monroe, "Loratadine in the Treatment of Urticaria," *Clinical Therapeutics*, 19(2), 232-242 (1997).††*
Knowles et al., "Astemizole and terfenadine-Induces Cardiovascular Effects," *Canadian Journal of Hospital Pharmacy*, 45(1), 33 & 37 (Feb. 1992).††*
Isselbacher et al.†† (eds.), *Harrison's Principles of Internal Medicine, Thirteenth Edition*, McGraw-Hill, Inc., New York, NY, 1994, only pp. 402-403 supplied.*
Estelle et al.††, "The Pharmacology and Use of $H_1$-Receptor-Antagonist Drugs," *The New England Journal of Medicine*, 330(23), 1665-1670 (Jun. 9, 1994).*
Berkow et al.†† (eds.), *The Merck Manual of Diagnosis and Therapy, Sixteenth Edition*, Merck & Co., Rahway, NJ, May 1992, only pp. 1262-1265 provided.*
Brandes et al.††, "Enhanced Cancer Growth in Mice Administered Daily Human-Equivalent Doses of Some $H_1$-Antihistamines: Predictive *in vitro* Correlates," *PubMed* (National Library of Medicine USA): PMID 7909571, published on line in 1994: only Abstract supplied.*
E. A. Swinyard (I), "Gastrointestinal Drugs," Chapter 39 in *Remington's Pharmaceutical Sciences, 18th Edition*, Gennaro et al. (eds.), Mack Publishing Co., Easton, PA, 1990, only pp. 774-799 supplied.*

(Continued)

*Primary Examiner*—Celia Chang
(74) *Attorney, Agent, or Firm*—Jones Day

(57) ABSTRACT

Methods are disclosed utilizing DCL, a metabolic derivative of loratadine, for the treatment of allergic rhinitis, and other disorders, while avoiding the concomitant liability of adverse side-effects associated with other non-sedating antihistamines.

2 Claims, No Drawings

OTHER PUBLICATIONS

E. A. Swinyard (II), "Histamine and Antihistamines," Chapter 59 in *Remington's Pharmaceutical Sciences, 18th Edition*, Gennaro et al. (eds.), Mack Publishing Co., Easton, PA, 1990, only pp. 1123-1131 supplied.*

Berkow et al. (eds.), The Merck Manual of Diagnosis and Therapy, 16th Edition, Merck Research Laboratories, Rahway, NJ, May 1992, only pp. 332-334 supplied.*

Gennaro et al. (eds.), Remington's Pharmaceutical Sciences, 18th Edition, Mack Publishing Co., Easton, PA, 1990, only pp. 678 and 1123-1124 (from Chs. 34 & 59, respectively) are supplied.*

Thomas et al. (eds.), Taber's Cyclopedic Medical Dictionary, 17th Illustrated Edition, F. A. Davis Company, Philadelphia, PA, 1993 only pp. 2091-2092 supplied.*

Bocian, R, "Hay Fever (Allergic Rhinitis): Current Management Approaches," Palo Alto Medical Foundation, Spring, 2000, see <http://www.pamf.org/health/toyourhealth/hayfever/html>.*

E. W. Monroe, "Loratadine in the Treatment of Urticaria," Clinical Therapeutics, 19(2), 232-242 (1997).*

Knowles et al., "Astemizole and Terfenadine-Induces Cardiovascular Effects," Canadian Journal of Hospital Pharmacy, 45(1), 33 &37 (Feb. 1992).*

Isselbacher et al. (eds.), HarrisonÖs Principles of Internal Medicine, Thirteenth Edition, McGraw-Hill, Inc., New York, NY, 1994, only pp. 402-403 supplied.*

Estelle et al., "The Pharmacology and Use of H1-Receptor-Antagonist Drugs," The New England Journal of Medicine, 330(23), 1665-1670 (Jun. 9, 1994).*

Berkow et al. (eds.), The Merck Manual of Diagnosis and Therapy, Sixteenth Edition, Merck & Co., Rahway, NJ, May 1992, only pp. 1262-1265 provided.*

Brandes et al., "Enhanced Cancer Growth in Mice Administered Daily Human-Equivalent Doses of Some H1-Antihistamines; Predictive in vitro Correlates" PubMed (National Library of Medicine USA): PMID 7909571, published on line in 1994: only Abstract.*

E. A. Swinyard (I), "Gastrointestinal Drugs," Chapter 39 in Remington's Pharmaceutical Sciences, 18th Edition, Gennaro et al. (eds.), Mack Publishing Co., Easton, PA, 1990, only pp. 774-799 supplied).*

E. A. Swinyard (II), "Histamine and Antihistamines," Chapter 59 in Remington's Pharmaceutical Sciences, 18th Edition, Gennaro et al. (eds.), Mack Publishing Co., Easton, PA, 1990, only pp. 1123-1131 supplied.*

Brandes et al. (II), "Enhanced Cancer Growth in Mice Administered Daily Human-Equivalent Doses of Some H1-Antihistamines: Predictive in vitro Correlates," Journal of the National Cancer Institute, 86(10), 770-775 (May 18, 1994).*

S. L. Nightingale, "Warning Issued on Nonsedating Antihistamines Terfenadine and Astemizole," Journal of the American Medical Association, 268(6), 705 (Aug. 12, 1992).*

Berthon et al., "In Vitro Inhibition by Loratadine and Descarbethoxy-Ioratadine, of Histamine Release from Human Basophils, and . . . (RBL-2H3)," Biochemical Pharmacology, 47(5), 789-794 (1994).*

J. F. Wiley II, et al., "Cardiotoxic Effects of Astemizole Overdose in Children," Journal of Pediatrics, 120(5), 799-802 (May 1992).*

A. Van Peer et al., "Keloconazole Inhibits Loratadine Metabolism in Man," European Journal of Allergy & Clinical Immunology, 48(Suppl. 16), 34, 1993: Derwent Abstract Accessio No.: 93-55671; only abstract supplied.*

C. I. Ezeamuzie et al., "Effect of Histamine H2-Receptor Antagonists on Acute Inflammatory of the Rat Paw Oedema," J. Pharm. Pharmacol., 41, 261-265 (1989).*

K. Kyuki et al., "Topical Anti-Inflammatory Activity of Dexamethasone 17-Valerate," Nippon Yakurigaku Zasshi 77(1), 73-85 (Jan. 1981); Pub Med Abstract/Translation from Japanese, PMID 7262708; only Abstract supplied.*

S. Kawaguchi et al., "Nasal Mast Cell in Experimentally Induced Allergic Rhinitis in Guinea-Pigs," Clinical and Experimental Allergy, 24, 238-244 (1994).*

T. Abe et al., "Antiallergic Effects of ZCR-2060: Effect on Allergic Cutaneous Reactions and Rhinitis Models in Mice and Rats," Japanese Journal of Pharmacology, 66, 95-103 (1994).*

A. G. Gilman et al. (I, eds.), Goodman & Gilman's The Pharmacological Basis of Therapeutics, Eighth Edition, Pergamon Press, New York, NY, 1990, only pp. 7, 197-199 and 582-588 supplied.*

A. G. Gilman et al. (II, eds.), Goodman & Gilman's The Pharmacological Basis of Therapeutics, Ninth Edition, Pergamon Press, New York, NY, 1996, only p. 588 supplied.*

A. P. Good et al., "Loratadine and Ventricular Tachycardia," Journal of Cardiology, 74(15), 207 (1994).*

K. Nyman et al., "Serious Side Effects of the Antiallergic Loratadine—Warning Against Long-term Use of Non-Prescription Preparation," Lakartidningen, 99(25), 2281 (1992); only English translation provided.*

R. W. Brimblecomb et al., "The Pharmacology of Burimamide and Metiamide, Two Histamine H2 Receptor Antagonists," Federation Proceedings, 35(8), 1931-1934 (Jun. 1976).*

N. Takahashi et al., "Allergic Rhinitis Model with Brown Norway Rat and Evaluation of Antiallergic Drugs," Journal Pharmacobio-Dyn., 13, 414-420 (1990).*

Merck Index; 12th Edition, Merck & Co., Rahway, NJ, 1990, only pp. 132, 892, 5611 and 9307 supplied.*

H. G. Mandel, "Pathways of Drug Biotransformation: Biochemical Conjugates," Chaper 10 in Fundamentals of Drug Metabolism and Drug Deposition, Williams & Wilkins, Baltimore, MD, 1971, only pp. 149-151 supplied.*

Incomplete cite.*

Incomplete cite.*

R. L. Woolsey et al., "Effects of Astemizole and Its Metabolites on Cardiac Repolarization," Georgetown University Document No. AST-2, Georgetown University, Washington, D.C., 1995; see also Sepracor Document No. 110-408.*

R. Arky et al. (eds.), Physician's Desk Reference, 1994 Edition, Medical Economics Data Production Company, Montvale, NJ, only pp. 1087-1090 supplied.*

A. G. Gilman et al. (III, eds.), Goodman & Gilman's The Pharmacological Basis of Therapeutics, Ninth Edition, Pergamon Press, New York, NY, 1996, only p. 590 supplied.*

EPO Oral Proceeding, written record of Refusal of an EP Patent Application for EP Application No. 95 943 722.9-2112, Sep. 8, 2000, see entire document.*

Atsushi et al. "Loratadine in treating urtiteria . . . " J. Clin. therapeutics and Med. 6(12) 2689-2705 (1990).*

Hilbert et al. "Pharmacokinetics . . . " CA 108:31237 (1988).*

Notari et al. "Biopharmaceutics . . . " Marcel Dekker, p. 163-164 (1975).*

Garattini "Active drug metabolites . . . " Clin. pHarm. v. 10, p. 216-227 (1985).*

Shareeah A. "Comparative efficacy of loratadine . . . " Intm, Dermatology, v. 31(5), p. 355-356 (1992).*

Sepracor "Fact sheet" 2006, p. 1-4.*

Berkow et al. (I, eds.), *The Merck Manual of Diagnosis and Therapy, 16th Edition*, Merck Research Laboratories, Rahway, NJ, May 1992, only pp. 332-334 supplied.

Gennaro et al. (eds.), *Remington's Pharmaceutical Sciences, 18th Edition*, Mack Publishing Co., Easton, PA, 1990, only pp. 678 and 1123-1124 (from Chs. 34 & 59, respectively) are supplied.

Thomas et al. (eds.) *Taber's Cyclopedic Medical Dictionary, 17th Illustrated Edition*, F. A. Davis Company, Philadelphia, PA, 1993, only pp. 2091-2092 supplied.

Bocian, R, "Hay Fever (Allergic Rhinitis): Current Management Approaches," Palo Alto Medical Foundation, Spring, 2000, see <http://www.pamf.org/health/toyourhealth/hayfever/html>.

E. W. Monroe, "Loratadine in the Treatment of Urticaria," *Clinical Therapeutics, 19*(2), 232-242 (1997).††

Knowles et al., "Astemizole and Terfenadine-Induces Cardiovascular Effects," *Canadian Journal of Hospital Pharmacy, 45*(1), 33 & 37 (Feb. 1992).††

Isselbacher et al.†† (eds.), *Harrison's Principles of Internal Medicine, Thirteenth Edition*, McGraw-Hill, Inc., New York, NY, 1994, only pp. 402-403 supplied.

Estelle et al.††, "The Pharmacology and Use of H₁-Receptor-Antagonist Drugs," *The New England Journal of Medicine*, 330(23), 1665-1670 (Jun. 9, 1994).

Berkow et al.†† (II, eds.), *The Merck Manual of Diagnosis and Therapy, Sixteenth Edition*, Merck & Co., Rahway, NJ, May 1992, only pp. 1262-1265 provided.

Brandes et al. (I)††, "Enhanced Cancer Growth in Mice Administered Daily Human-Equivalent Doses of Some H₁-Antihistamines: Predictive *in vitro* Correlates," *PubMed* (National Library of Medicine USA): PMID 7909571, published on line in 1994: only Abstract supplied.

E. A. Swinyard (I), "Gastrointestinal Drugs," Chapter 39 in *Remington's Pharmaceutical Sciences, 18th Edition*, Gennaro et al. (eds.), Mack Publishing Co., Easton, PA, 1990, only pp. 774-799 supplied.

E. A. Swinyard (II), "Histamine and Antihistamines," Chapter 59 in *Remington's Pharmaceutical Sciences, 18th Edition*, Gennaro et al. (eds.), Mack Publishing Co., Easton, PA, 1990, only pp. 1123-1131 supplied.

Brandes et al. (II)††, "Enhanced Cancer Growth in Mice Administered Daily Human-Equivalent Doses of Some H₁-Antihistamines: Predictive *in vitro* Correlates," *Journal of the National Cancer Institute*, 86(10), 770-775 (May 18, 1994).

S. L. Nightingale††, "Warning Issued on Nonsedating Antihistamines Terfenadine and Astemizole," *Journal of the American Medical Association*, 268(6), 705 (Aug. 12, 1992).

Berthon et al.††, "*In Vitro* Inhibition, by Loratadine and Descarbethoxy-loratadine, of Histamine Release from Human Basophils, and of Histamine Release and Intracellular Calcium Fluxes in Rat Basophilic Leukemia Cells (RBL-2H3)," *Biochemical Pharmacology*, 47(5), 789-794 (1994).

J. F. Wiley II, et al.††, "Cardiotoxic Effects of Astemizole Overdose in Children," *Journal of Pediatrics*, 120(5), 799-802 (May 1992).

A. Van Peer et al.††, "Ketoconazole Inhibits Loratadine Metabolism in Man," *European Journal of Allergy & Clinical Immunology*, 48(Suppl. 16), 34, 1993: Derwent Abstract Accessio No. 93-55671; only abstract supplied.

C. I. Ezeamuzie et al.††, "Effect of Histamine H₂-Receptor Antagonists on Acute Inflammatory of the Rat Paw Oedema," *J. Pharm. Pharmacol.*, 41, 261-265 (1989).

K. Kyuki et al.††, "Topical Anti-Inflammatory Activity of Dexamethasone 17-Valerate," *Nippon Yakurigaku Zasshi*, 77(1), 73-85 (Jan. 1981); Pub Med Abstract/Translation from Japanese, PMID 7262708; only Abstract supplied.

S. Kawaguchi et al.††, "Nasal Mast Cell in Experimentally Induced Allergic Rhinitis in Guinea-Pigs," *Clinical and Experimental Allergy*, 24, 238-244 (1994).

T. Abe et al.††, "Antiallergic Effects of ZCR-2060: Effect on Allergic Cutaneous Reactions on Rhinitis Models in Mice and Rats," *Japanese Journal of Pharmacology*, 66, 95-103 (1994).

A. G. Gilman et al. (I, eds.),††, *Goodman & Gilman's The Pharmacological Basis of Therapeutics, Eighth Edition*, Pergamon Press, New York, NY, 1990, only pp. 7, 197-199 and 582-588 supplied.

A. G. Gilman et al. (II, eds.)††, *Goodman & Gilman's The Pharmacological Basis of Therapeutics, Ninth Edition*, Pergamon Press, New York, NY, 1996, only p. 588 supplied.

A. P. Good et al.††, "Loratadine and Ventricular Tachycardia," *Journal of Cardiology*, 74(15), 207 (1994).

K. Nyman et al.††, "Serious Side Effects of the Antiallergic Loratadine—Warning Against Long-Term Use of Non-Prescription Preparation," *Lakartidningen*, 99(25), 2281 (1992); only English translation provided.

R. W. Brimblecomb et al.††, "The Pharmacology of Burimamide and Metiamide, Two Histamine H₂ Receptor Antagonists," *Federation Proceedings*, 35(8), 1931-1934 (Jun. 1976).

N. Takahashi et al.††, "Allergic Rhinitis Model with Brown Norway Rat and Evaluation of Antiallergic Drugs," *Journal Pharmacobio-Dyn.*, 13, 414-420 (1990).

*Merck Index, 12th Edition*††, Merck & Co., Rahway, NJ, 1990, only pp. 132, 892, 5611 and 9307 supplied.

H. G. Mandel ††, "Pathways of Drug Biotransformation: Biochemical Conjugates," Chaper 10 in *Fundamentals of Drug Metabolism and Drug Deposition*, Williams & Wilkins, Baltimore, MD, 1971, only pp. 149-151 supplied.

R. L. Woolsey et al.††, "Effects of Astemizole and Its Metabolites on Cardiac Repolarization," Georgetown University Document No. AST-2, Georgetown University, Washington, D.C., 1995; see also Sepracor Document No. 110-408.

R. Arky et al. (eds.), *Physician's Desk Reference, 1994 Edition*,†† Medical Economics Data Production Company, Montvale, NJ, only pp. 1087-1090 supplied.

A. G. Gilman et al. (III, eds.)††, *Goodman & Gilman's The Pharmacological Basis of Therapeutics, Ninth Edition*, Pergamon Press, New York, NY, 1996, only p. 590 supplied.

EPO Oral Proceeding††, written record of Refusal of an EP Patent Application for EP Application No. 95 943 722.9-2112 Sep. 8, 2000, see entire document.

Babe et al., 1996, "Histamine, Bradykinin, and Their Antagonists", *Goodman & Gilman's The Pharmacological Basis of Therapeutics*, *9th ed*., pp. 581-593 and 598-599.

McCue, J., 1996, "Safety of Antihistamines in the Treatment of Allergic Rhinitis in Elderly Patients", Arch. Fam. Med. 5:464-468.

Andersen et al., 1995, "Adverse Drug Interactions Clinically Important for the Dermatologist", Arch. Dermatol. 131:468-473.

Peggs et al., 1995, "Antihistamines: The Old and The New", American Family Physician 52(2):593-600.

Berthon et al., 1994, "In Vitro Inhibition, by Loratadine and Descarboxyethoxloratadine, of Histamine Release from Human Basophils, and of Histamine Release and Intracellular Calcium Fluxes in Rat Basophilic Leukemia Cells (RBL-2H3)", Biochemical Pharmacology 47(5): 789-794.

Brandes et al., 1994, "Enhanced Cancer Growth in Mice Administered Daily Human-Equivalent Doses of Some H₁-Antihistamines: Predictive In Vitro Correlates", J. Nat. Can. Inst. Reports 86(10): 770-775.

Kleine-Tebbe et al., 1994, "Inhibition of IgE- and non-IgE-mediated histamine release from human basophil leukocytes in vitro by a histamine H₁-antagonist, desethoxycarbonyl-loratadine", J. Allergy Clin. Immunol. 93(2):494-500.

Miadonna et al., 1994, "Inhibitory Effect of the H₁ Antagonist Loratadine on Histamine Release from Human Basophils", Int. Arch. Allergy Immunol. 105:12-17.

Simons, F.E.R., 1994, "H₁-Receptor Antagonists Comparative Tolerability and Safety", Drug Safety 10(5):350-380.

Zhong et al., 1994, "HPLC-Bestimmung Von Loratadin und seinem aktiven Metaboliten Descarboethoxyloratadin in Humanplasma", Pharmazie 49(10):736-739 (English abstract attached).

Quercia et al., 1993, "*Focus on loratadine*: A new second-generation nonsedating H₁-receptor antagonist", Hosp. Formul. 28:137-149,153.

Lavrijsen et al., 1993, "The Interaction of Ketoconazole, Itraconazole and Erthromycin With the In Vitro Metabolism of Antihistamines in Human Liver Microsomes", Abstract 1233 Eur. J. Allergy Clin Immunol. 48(Suppl. 16):34.

Roman et al., 1993, "Loratadine A Review of Recent Findings in Pharmacology, Pharmacokinetics, Efficacy, and Safety, with a Look at its Use in Combination with Pseudoephedrine", Clinical Reviews in Allergy 11:89-110.

Van Peer et al., 1993, "Ketoconazole Inhibits Loratadine Metabolism in Man", Abstract 1234 Eur. J. Allergy Clin. Immunol. 48(Suppl. 16):34.

Product Insert CR-318/17597400 7/93 Schering Corporation (1992, 1993).

Brandes et al., 1992, "Stimulation of Malignant Growth in Rodents by Antidepressant Drugs at Clinically Relevant Doses", Cancer Research 52:3796-3800.

Kaliner, M., 1992, "Nonsedating Antihistamines: Pharmacology, Clinical Efficacy and Adverse Effects", American Family Physician 45(3):1337-1342.

Knowles, 1992, "Astemizole and Terfenadine—Induced Cardiovascular Effects", Canadian J. Hosp. Pharm. 45(1):33, 37.

Parkinson et al., 1992, "Evaluation of Loratadine as an Inducer of Liver Microsomal Cytochrome P450 in Rats and Mice", Biochemical Pharmacology 43(10):2169-2180.

Van Cauwenberge, P., 1992, "New Data on the Safety of Loratadine", Drug Invest. 4(4):283-291.

Barnett et al., 1991, "Pharmacology of Non-Sedating $H_1$ Antihistamines", New Perspectives in Histamine Research pp. 181-196.

"Antihististamines", 1990, Chapter 16 Side Effects of Drugs Annual 14:135-138 Elsevier Science Publishers.

Gengo, F.M, 1990, "Delimma: Antihistamine Selection: Use vs. Side Effects", U.S. Pharmacist pp. 59-72, 92.

Clissold et al., 1989, "Loratadine A Preliminary Review of its Pharmacodynamic Properties and Therapeutic Efficacy", Drugs 37:42-57.

"Antihististamines", 1988, Chapter 16 Side Effects of Drugs Annual 12:142-143 Elsevier Science Publishers.

Simons et al., 1988, "Astemizole—Induced Torsades de Pointes", Lancet p. 624.

Temple et al., 1988, "Loratadine, as Antihistamine, Blocks antigen- and Ionophore—Induced Leukotriene Release From Human Lung In Vitro", Prostaglandins 35(4):549-554.

Hilbert et al., 1987, "Pharmacokinetics and Dose Proportionality of Loratadine", J. Clin. Pharmacol. 27:694-698.

Craft, 1986, "Torsade de Pointes After Astemizole Overdose", British Med. J. 292:660.

Barnett et al., 1984, "Evaluation of the CNS properties of SCH 29851, a potential non-sedating antihistamine", Agents and Actions 14(5/6):590-597.

Wood, 1979, "Antimotion Sickness and Antiemetic Drugs", Drugs 17(17):471-479.

Cohen et al., 1972, "Meclizine and Placebo in Treating Vertigo of Vestibular Origion", Arch. Neurol. 27:129-135.

Goodman & Gilman's, 1996, The Pharmacological Basis of Therapeutics, 9th Ed. p. 148, 588-592.

Carmeliet, 1992, "Voltage- and Time-Dependent Block of the Delayed $K^+$ Current in Cardiac Myocytes by Dofetilide", J. Pharmacol. Exper. Ther. 262:809-817.

Lunde, I., 1990, "Antihistamines", Side Effects of Drugs 14:135-138.

Dukes, M.N.G. et al., 1988, "Side Effects of Drugs Annual 12", Elsevier Science Publishers B.V. pp. 142-143.

Ebert, W., 1977, "Soft Elastic Gelatin Capsules: A Unique Dosage Form", Pharmaceutical Technology 1:44-50.

Petrin, A., 1974, "Motion Sickness and its Treatment", Schweiz. Med. 63:79-81.

Wood, C.D. et al.,, 1987, "Mechanisms of Antimotion Sickness Drugs", Aviation, Space, and Envir. Med. pp. A262-A265.

Roquet, A., et al., "Combined Antagonism of Leukotriene and Histamine Produces Predominant Inhibition of Allergen-Induced Early and Late Phase Airway Obstruction in Asthmatics", Am. J. Respir. Crit. Care Med., 155:1856-1863 (1997).

McClintock et al., "Skin Reactions and Terfenadine," New Zealand Medical Journal, 1995, 108, 208(May 24, 1995).

Michel, M, "Skin Reactions to Hydroxyzine", Dept. of Dermatology of Caen, France, vol. 36:147-149 (1997).

Monroe, "Loratidine in the Treatment of Uriticaria," Clinical Therapeutics, 1997, 19, 232-242.

Parslew, R., "Warfarin Treatment of Chronic Idiopathic Urticaria and Angio-oedema", Clinical. And Experimental Allergy, vol. 30: 1161-1165 (2000).

Simons et al., "The Pharmacology and Use of H1 Receptor-Antagonist Drugs", New England Journal of Medicine 1994, 330, 1663—1670 (Jun. 9, 1994).

Yap, Y., "The Current Cardiac Safety Situation with Antihistamines", Clinical and Experimental Allergy, vol. 29, Suppl. 1: 15-24 (1999).

Clissold et al., 1989, "Loratadine A Preliminary Review of its Pharmacodynamic Properties and Therapeutic Efficacy", Drugs 37:42-57.

Simons et al., 1988, "Astemizole—Induced Torsades de Pointes", Lancet, 624.

Temple et al., 1988, "Loratadine, an Antihistamine, Blocks antigen- and Ionophore—Induced Leukotriene Release From Human Lung In Vitro", Prostaglandins, 35(4):549-554.

Hilbert et al., 1987, "Pharmacokinetics and Dose Proportionality of Loratadine", J. Clin. Pharmacol., 27:694-698.

Craft, 1986, "Torsade de Pointes After Astemizole Overdose", British Med. J., 292: 660.

Barnett et al., 1984, "Evaluation of the CNS properties of SCH 29851, a potential non-sedating antihistamine", Agents and Actions, 14(5/6):590-597.

Wood, 1979, "Antimotion Sickness and Antiemetic Drugs", Drugs, 17(17):471-479.

Cohen et al., 1972, "Meclizine and Placebo in Treating Vertigo of Vestibular Origion", Arch. Neurol., 27:129-135.

Goodman and Gilman's, 1996, The Pharmacological Basis of Therapeutics, 9th Ed. p. 148, 588-592.

Carmeliet, 1992, "Voltage- and Time-Dependent Block of the Delayed $K^+$ Current in Cardiac Myocytes by Dofetilide", J. Pharmacol. Exper. Ther., 262:809-817.

Lunde, I., 1990, "Antihistamines", Side Effects of Drugs, 14:135-138.

Dukes, M.N.G. et al., 1988, "Side Effects of Drugs Annual 12", Elsevier Science Publishers B.V.; pp. 142-143.

Ebert, W., 1977, "Soft Elastic Gelatin Capsules: A Unique Dosage Form", Pharmaceutical Technology, 1:44-50.

Petrin, A., 1974, "Motion Sickness and Its Treatment", Schweiz. Med., 63:79-81.

Wood, C.D. et al.,, 1987, "Mechanisms of Antimotion Sickness Drugs", Aviation, Space, and Envir. Med., pp. A262-A265.

"Antihistamines General Statement," printout from Medscape website (http://promini.medscape.com), date unknown.

Heithoff et al., J. Allergy Clin. Immuno., 104(1): S383-4, Abstract No. 1121 (1999).

Nayak et al., J. Allergy. Clin. Immuno., 104(1): S384, Abstract No. 1122 (1999).

Salmun et al., J. Allergy. Clin. Immuno., 104(1): S384-5, Abstract No. 1123 (1999).

* cited by examiner

METHODS FOR TREATING URTICARIA USING DESCARBOETHOXYLORATADINE

The present invention is a division of application Ser. No. 09/039,260, filed Mar. 16, 1998, which is a division of application Ser. No. 08/783,393, filed Jan. 13, 1997, now U.S. Pat. No. 5,731,319, which is a division of application Ser. No. 08/366,651, filed Dec. 30, 1994, now U.S. Pat. No. 5,595,997

1. BACKGROUND OF THE INVENTION

The methods of the present invention comprise administering a therapeutically effective amount of a metabolic derivative of loratadine. Chemically, this derivative is 8-chloro-6,11-dihydro-11-(4-piperidylidene)-5H-benzo[5,6]cyclohepta[1,2-b]pyridine and known as descarboethoxyloratadine (DCL). This compound is specifically described in Quercia, et al. *Hosp. Formul.*, 28: 137–53 (1993) and U.S. Pat. No. 4,659,716.

Loratadine is an antagonist of the H-1 histamine receptor protein. The histamine receptors H-1 and H-2 are two well-identified forms. The H-1 receptors are those that mediate the response antagonized by conventional antihistamines. H-1 receptors are present, for example, in the ileum, the skin, and the bronchial smooth muscle of man and other mammals.

Loratadine binds preferentially to peripheral rather than to central H-1 receptors. Quercia et al., *Hosp. Formul.* 28: 137–53 (1993). Loratadine has been shown to be a more potent inhibitor of serotonin-induced bronchospasm in guinea pigs than terfenadine. Id. at 137–38. Its anti-allergenic activity in animal models was shown to be comparable to that of terfenadine and astemizole. Id. at 138. However, using standard animal model testing, on a milligram by milligram basis, loratadine was shown to be four times more potent than terfenadine in the inhibition of allergic bronchospasm. Id. Moreover, loratadine's antihistaminic activity was demonstrated in humans by evaluation of the drug's ability to suppress wheal formation. Id. Clinical trials of efficacy indicated that loratadine is an effective H-1 antagonist. See Clissold et al., *Drugs* 37: 42–57 (1989).

Through H-2 receptor-mediated responses, histamine stimulates gastric acid secretion in mammals and the chronotropic effect in isolated mammalian atria. Loratadine has no effect on histamine-induced gastric acid secretion, nor does it alter the chronotropic effect of histamine on atria. Thus, loratadine has no apparent effect on the H-2 histamine receptor.

Loratadine is well absorbed but is extensively metabolized. Hilbert, et al., *J. Clin. Pharmacol.* 27: 694–98 (1987). The main metabolite, DCL, which has been identified, is reported to be pharmacologically active. Clissold, *Drugs* 37: 42–57 (1989). It is also reported as having antihistaminic activity in U.S. Pat. No. 4,659,716. This patent recommends an oral dosage range of 5 to 100 mg/day and preferably 10 to 20 mg/day.

Loratadine's efficacy in treating seasonal allergic rhinitis is comparable to that of terfenadine. Quercia et al., *Hosp. Formul.* 28: 137, 141 (1993). Loratadine also has a more rapid onset of action than astemizole. Id.

Clissold et al., *Drugs* 37: 42, 50–54 (1989) describes studies showing loratadine as effective for use in seasonal and perennial rhinitis, colds (with pseudoephedrine), and chronic urticaria. It has also been suggested that loratadine would be useful for the treatment of allergic asthma. Temple et al. *Prostaglandins* 35:549–554 (1988).

Loratadine may also be useful for the treatment of motion sickness and vertigo. Some antihistamines have been found to be effective for the prophylaxis and treatment of motion sickness. See Wood, *Drugs,* 17: 471–79 (1979). Some antihistamines have also proven useful for treating vestibular disturbances, such as Meniere's disease, and in other types of vertigo. See Cohen et al., *Archives of Neurology,* 27: 129–35 (1972).

In addition, loratadine may be useful in the treatment of diabetic retinopathy and other small vessel disorders associated with diabetes mellitus. In tests on rats with streptozocin-induced diabetes, treatment by antihistamines prevented the activation of retinal histamine receptors which have been implicated in the development of diabetic retinopathy. The use of antihistamines to treat retinopathy and small vessel disorders associated with diabetes mellitus is disclosed in U.S. Pat. No. 5,019,591.

It has also been suggested that loratadine, in combination with non-steroidal antiinflammatory agents or other non-narcotic analgesics, would be useful for the treatment of cough, cold, cold-like and/or flu symptoms and the discomfort, pain, headache, fever, and general malaise associated therewith. Such compositions used in the methods of treating the above-described symptoms may optionally include one or more other active components including a decongestant (such as pseudoephedrine), a cough suppressant/antitussive (such as dextromethorphan) or an expectorant (such as guaifenesin).

Many antihistamines cause adverse side-effects. These adverse side-effects include, but are not limited to, sedation, gastrointestinal distress, dry mouth, constipation or diarrhea. Loratadine has been found to cause relatively less sedation as compared with other antihistamines. Moreover, the incidence of fatigue, headache, and nausea was similar to those observed for terfenadine. See Quercia et al., *Hosp. Formul.* 28: 137,142 (1993).

Furthermore, compounds within the class of non-sedating antihistamines, including loratadine, astemizole, and terfenadine, have been known to cause other severe adverse electrophysiologic side-effects. These adverse side-effects are associated with a prolonged QT interval and include but are not limited to ventricular fibrillation and cardiac arrhythmias, such as ventricular tachyarrhythmias or torsades de pointes. Knowles, *Canadian Journal Hosp. Pharm.,* 45: 33,37 (1992); Craft, *British Medical Journal,* 292: 660 (1986); Simons et al., *Lancet,* 2: 624 (1988); and Unknown, *Side Effects of Drugs Annual,* 12: 142 and 14: 135.

Quercia et al., *Hosp. Formul.* 28: 137, 142 (1993) noted that serious cardiovascular adverse side-effects, including torsades de pointes and other ventricular arrhythmias, were reported in "healthy" patients who received terfenadine concurrently with either ketoconazole or erythromycin. Quercia et al., also states that arrhythmias have also been reported with the concomitant administration of astemizole and erythromycin or erythromycin plus ketoconazole. Thus, he cautions against using loratadine concurrently with ketoconazole, itraconazole, and macrolides, such as erythromycin.

Additionally, it is also known that ketoconazole and/or erythromycin interfere with cytochrome P450, and thereby inhibit the metabolism of non-sedative antihistamines such as terfenadine and astemizole. Because of the interference with the metabolism of loratadine, there exists a greater potential for adverse interaction between loratadine or other non-sedating antihistamines and drugs known to inhibit cytochrome P450, such as but not limited to ketoconazole, itraconazole, and erythromycin.

In Brandes et al., *Cancer Res.* (52) 3796–3800 (1992), Brandes showed that the propensity of drugs to promote tumor growth in vivo correlated with potency to inhibit concanavalin A stimulation of lymphocyte mitogenesis. In Brandes et al., *J. Nat'l Cancer Inst.*, 86:(10) 771–775 (1994), Brandes assessed loratadine in an in vitro assay to predict enhancement of in vivo tumor growth. He found that loratadine and astemizole were associated with growth of both melanoma and fibrosarcoma tumors. The dose for loratadine in this study was 10 mg/day.

None of the above references teach or enable the methods of the present invention comprising administering DCL to a human while avoiding adverse side-effects associated with the administration of other non-sedating antihistamines; nor do the references alone or in combination suggest these methods. Thus, it would be particularly desirable to find methods of treatment with the advantages of known non-sedating antihistamines which would not have the aforementioned disadvantages.

2. SUMMARY OF THE INVENTION

It has now been discovered that DCL is an effective, non-sedating antihistamine which is useful in treating allergic rhinitis in a human, while avoiding adverse side-effects normally associated with the administration of other compounds within the class of non-sedating antihistamines such as loratadine, astemizole, and terfenadine. Such adverse side-effects include, but are not limited to, cardiac arrhythmias, cardiac conduction disturbances, fatigue, headache, gastrointestinal distress, appetite stimulation, weight gain, dry mouth, and constipation or diarrhea.

Furthermore, DCL is useful for treating allergic rhinitis while avoiding tumor promotion associated with loratadine and other non-sedating antihistamines. Thus, this invention also relates to novel methods of treating allergic rhinitis in a human having a higher than normal propensity for or incidence of cancer.

Furthermore, it has now also been discovered that DCL, is useful in treating allergic asthma in a human, while avoiding the adverse side-effects associated with the administration of other non-sedating antihistamines. As stated above, examples of such side-effects are appetite stimulation, weight gain, tumor promotion, cardiac arrhythmias, and cardiac conduction disturbances. Thus, this invention also relates to novel methods of treating allergic asthma in a human having a higher than normal propensity for or incidence of cancer.

In addition, DCL is useful in treating such disorders in a human as retinopathy and small vessel disorders associated with diabetes mellitus while avoiding the adverse side-effects associated with administration of other non-sedating antihistamines and while avoiding tumor promotion associated with the administration of loratadine and other non-sedating antihistamines. Thus, this invention also relates to novel methods of treating retinopathy and small vessel disorders associated with diabetes mellitus, in a human having a higher than normal propensity for or incidence of cancer.

It has also been discovered that DCL, in combination with non-steroidal antiinflammatory agents or other non-narcotic analgesics, is useful for the treatment of cough, cold, cold-like and/or flu symptoms and the discomfort, pain, headache, fever, and general malaise associated therewith in a human, while avoiding the adverse side-effects associated with the administration of other non-sedating antihistamines. The use of such pharmaceutical compositions, containing DCL, and non-narcotic analgesics or non-steroidal antiinflammatory agents such as aspirin, acetaminophen or ibuprofen, may optionally include one or more other active components including a decongestant (such as pseudoephedrine), a cough suppressant/antitussive (such as dextromethorphan) or an expectorant (such as guaifenesin).

The present invention also involves the use of the above-described compositions to treat the above-described conditions while avoiding tumor promotion associated with loratadine and other non-sedating antihistamines. Thus, the present invention also relates to the use of these compositions to treat such conditions in a human having a higher then normal propensity for or incidence of cancer.

The present invention also relates to a method of avoiding interaction between DCL and a drug that inhibits cytochrome P450 including but not limited to ketoconazole, itraconazole, erythromycin, and others known by those skilled in the art, while treating allergic rhinitis, allergic asthma, diabetic retinopathy and other small vessel disorders due to diabetes.

This invention is also directed to a method of avoiding interaction between DCL and a drug that inhibits cytochrome P450 including but not limited to ketoconazole, itraconazole, erythromycin, and others known to those skilled in the art, while treating cough, cold, cold-like and/or flu symptoms and the discomfort, headache, pain, fever and general malaise associated therewith, in a human, which comprises administering a composition to said human, said composition comprising DCL and a non-steroidal antiinflammatory agent or non-narcotic analgesic. The aforementioned compositions may optionally contain one or more other active components including a decongestant, cough suppressant/antitussive, or expectorant.

It has also been discovered that DCL is useful in treating other allergic disorders related to its activity as an antihistamine, including but not limited to, urticaria and symptomatic dermographism, in a human, while avoiding the adverse side-effects associated with the administration of other non-sedating antihistamines and/or while avoiding tumor promotion associated with the administration of loratadine and other non-sedating antihistamines. Thus, this invention also relates to novel methods of treating allergic disorders, including but not limited to, urticaria and symptomatic dermographism in a human having a higher than normal propensity for or incidence of cancer. The present invention also relates to methods of avoiding interaction between loratadine or other non-sedating antihistamines and a drug that inhibits cytochrome P450 including but not limited to ketoconazole, itraconazole, and erythromycin, and others known by those skilled in the art, while treating allergic disorders, including but not limited to, urticaria and symptomatic dermographism wherein said human is administered DCL.

3. DETAILED DESCRIPTION OF THE INVENTION

The present invention encompasses a method of treating allergic rhinitis in a human while avoiding the concomitant liability of adverse side-effects associated with the administration of non-sedating antihistamines, which comprises administering to said human a therapeutically effective amount of DCL or a pharmaceutically acceptable salt thereof.

The present invention further encompasses a method of treating allergic asthma in a human while avoiding the concomitant liability of adverse side-effects associated with the administration of non-sedating antihistamines, which comprises administering to said human a therapeutically effective amount of DCL or a pharmaceutically acceptable salt thereof.

Also included in the present invention is a method of treating retinopathy or other small vessel diseases associated with diabetes mellitus in a human while avoiding the concomitant liability of adverse side-effects associated with the administration of non-sedating antihistamines, which comprises administering to said human a therapeutically effective amount of DCL or a pharmaceutically acceptable salt thereof.

The present invention further encompasses a method of treating cough, cold, cold-like, and/or flu symptoms and the discomfort, headache, pain, fever, and general malaise associated therewith, in a human, while avoiding the concomitant liability of adverse side-effects associated with the administration of non-sedating antihistamines, which comprises administering to said human a composition, said composition comprising (i) a therapeutically effective amount of DCL or a pharmaceutically acceptable salt thereof and (ii) a therapeutically effective amount of at least one non-steroidal antiinflammatory agent or non-narcotic analgesic such as acetylsalicylic acid, acetaminophen, ibuprofen, ketoprofen, and naproxen, or a pharmaceutically acceptable salt thereof.

Additionally, the present invention encompasses a method of treating cough, cold, cold-like, and/or flu symptoms and the discomfort, headache, pain, fever, and general malaise associated therewith, in a human, while avoiding the concomitant liability of adverse side-effects associated with the administration of non-sedating antihistamines, which comprises administering to said human a composition, said composition comprising (i) a therapeutically effective amount of DCL or pharmaceutically acceptable salt thereof, and (ii) a therapeutically effective amount of a decongestant such as pseudoephedrine or a pharmaceutically acceptable salt thereof.

It has been found that DCL is five to seven times less active in tumor promotion than loratadine. Thus, the present invention further encompasses a method of treating allergic rhinitis in a human while avoiding the concomitant liability of tumor promotion associated with the administration of loratadine and other non-sedating antihistamines, which comprises administering to said human a therapeutically effective amount of DCL or a pharmaceutically acceptable salt thereof.

A further aspect of the present invention includes a method of treating allergic asthma in a human while avoiding the concomitant liability of tumor promotion associated with the administration of loratadine and other non-sedating antihistamines, which comprises administering to said human a therapeutically effective amount of DCL or a pharmaceutically acceptable salt thereof.

The present invention further encompasses a method of treating retinopathy or other small vessel diseases associated with diabetes mellitus in a human while avoiding the concomitant liability of tumor promotion associated with the administration of loratadine and other non-sedating antihistamines, which comprises administering to said human a therapeutically effective amount of DCL or a pharmaceutically acceptable salt thereof.

Because DCL is much less active than loratadine at promoting tumors, a further aspect of this invention is a method of treating allergic rhinitis in a human wherein said human has a higher than normal propensity for or incidence of cancer, which comprises administering to said human a therapeutically effective amount of DCL or a pharmaceutically acceptable salt thereof.

The present invention further encompasses a method of treating allergic asthma in a human wherein said human has a higher than normal propensity for or incidence of cancer, which comprises administering to said human a therapeutically effective amount of DCL or a pharmaceutically acceptable salt thereof.

Also included in the present invention is a method for treating retinopathy or other small vessel diseases associated with diabetes mellitus in a human wherein said human has a higher than normal propensity for or incidence of cancer, which comprises administering to said human a therapeutically effective amount of DCL or a pharmaceutically acceptable salt thereof.

Furthermore, the present invention also includes a method of treating cough, cold, cold-like, and/or and flu symptoms and the discomfort, headache, pain, fever and general malaise associated therewith, in a human, wherein said human has a higher than normal propensity for or incidence of cancer, which comprises administering to said human a composition, said composition comprising (i) a therapeutically effective amount of DCL or a pharmaceutically acceptable salt thereof, and (ii) a therapeutically effective amount of a non-steroidal antiinflammatory agent or non-narcotic analgesic such as acetylsalicylic acid, acetaminophen, ibuprofen, ketoprofen, and naproxen, or a pharmaceutically acceptable salt thereof.

Moreover, the present invention further encompasses a method of treating cough, cold, cold-like and/or flu symptoms and the discomfort, headache, pain, fever and general malaise associated therewith, in a human, wherein said human has a higher than normal propensity for or incidence of cancer, which comprises administering to said human a composition, said composition comprising (i) a therapeutically effective amount of DCL or a pharmaceutically acceptable salt thereof, and (ii) a therapeutically effective amount of a decongestant such as pseudoephedrine or a pharmaceutically acceptable salt thereof.

It has also been found that when DCL is concurrently administered with a drug that inhibits cytochrome P450 including but not limited to ketoconazole, itraconazole, erythromycin and others known by those skilled in the art, the interaction between said DCL and said drug is decreased in comparison to the concurrent administration of loratadine or other non-sedating antihistamines with said drug.

Therefore, this invention also encompasses a method of avoiding interaction between DCL and a drug that inhibits cytochrome P450 including but not limited to ketoconazole, itraconazole, erythromycin and others known by those skilled in the art, while treating allergic rhinitis in a human, wherein said human is administered DCL or a pharmaceutically acceptable salt thereof.

Moreover, this invention also encompasses a method of avoiding interaction between loratadine or other non-sedating antihistamines and a drug that inhibits cytochrome P450 including but not limited to ketoconazole, itraconazole, erythromycin and others known by those skilled in the art, while treating allergic asthma in a human, wherein said human is administered DCL or a pharmaceutically acceptable salt thereof.

This invention also encompasses a method of avoiding interaction between DCL and a drug that inhibits cytochrome P450 including but not limited to ketoconazole, itraconazole, erythromycin and others known by those skilled in the art, while treating retinopathy or other small vessel diseases associated with diabetes mellitus in a human, wherein said human is administered DCL or a pharmaceutically acceptable salt thereof.

Also encompassed by the present invention is a method of avoiding interaction between DCL and a drug that inhibits cytochrome P450 including but not limited to ketoconazole, itraconazole, erythromycin and others known by those skilled in the art, while treating cough, cold, cold-like, and/or flu symptoms and the discomfort, headache, pain, fever and general malaise associated therewith, in a human, which comprises administering to said human a composition, said composition comprising (i) a therapeutically effective amount of DCL or a pharmaceutically acceptable salt thereof, and (ii) a therapeutically effective amount of a non-steroidal antiinflammatory agent or non-narcotic analgesic, such as acetylsalicylic acid, acetaminophen, ibuprofen, ketoprofen, and naproxen, or a pharmaceutically acceptable salt thereof.

A further aspect of the invention is a method of avoiding interaction between DCL and a drug that inhibits cytochrome P450 including but not limited to ketoconazole, itraconazole, erythromycin and others known by those skilled in the art, while treating cough, cold, cold-like, and/or flu symptoms and the discomfort, headache, pain, fever and general malaise associated therewith, in a human, which comprises administering to said human a composition, said composition comprising (i) a therapeutically effective amount of DCL or a pharmaceutically acceptable salt thereof, and (ii) a therapeutically effective amount of a decongestant such as pseudoephedrine or a pharmaceutically acceptable salt thereof.

A further aspect of this invention includes a method of treating urticaria in a human while avoiding the concomitant liability of adverse side-effects associated with the administration of non-sedating antihistamines, comprising administering to said human a therapeutically effective amount of DCL or a pharmaceutically acceptable salt thereof.

Furthermore, the present invention includes a method of treating symptomatic dermographism in a human while avoiding the concomitant liability of adverse side-effects associated with the administration of non-sedating antihistamines, comprising administering to said human a therapeutically effective amount of DCL or a pharmaceutically acceptable salt thereof.

It has also now been found that DCL is at least about twenty times more potent at the histamine receptor when compared to loratadine. Thus, the dosage range by the modes of administration described herein and for use in the methods of the present invention, are about 0.1 to less than about 10 mg per day. This is significantly lower than what has been recommended for other non-sedating antihistamines, including loratadine which has a recommended oral dose of 5 to 100 mg per day. However, due to the significantly less side-effects, DCL can be given in doses higher than those suggested for loratadine thereby offering an improved therapeutic range than loratadine.

Loratadine and other non-sedating antihistamines have antihistaminic activity and provide therapy and a reduction of symptoms for a variety of conditions and disorders related to allergic rhinitis and other allergic disorders, diabetes mellitus and other conditions; however, such drugs, while offering the expectation of efficacy, causes adverse side-effects. Utilizing DCL results in clearer dose-related definitions of efficacy, diminished adverse side-effects, and accordingly, an improved therapeutic index. It is, therefore, more desirable to use DCL than to use loratadine itself or other non-sedating antihistamines.

The term "adverse effects" includes, but is not limited to cardiac arrhythmias, cardiac conduction disturbances, appetite stimulation, weight gain, sedation, gastrointestinal distress, headache, dry mouth, constipation, and diarrhea. The term "cardiac arrhythmias" includes, but is not limited to ventricular tachyarrhythmias, torsades de pointes, and ventricular fibrillation.

The phrase "therapeutically effective amount" means that amount of DCL which provides a therapeutic benefit in the treatment or management of allergic rhinitis and other allergic disorders such as urticaria, symptomatic dermographism, allergic asthma, retinopathy or other small vessel disorders associated with diabetes mellitus, and the symptoms associated with allergic rhinitis such as cough, cold, cold-like, and/or flu symptoms including, but not limited to, sneezing, rhinorrhea, lacrimation, and dermal irritation.

The term "allergic asthma" is defined as a disorder characterized by increased responsiveness of the trachea and bronchi to various stimuli which results in symptoms which include wheezing, cough, and dyspnea.

The term "diabetic retinopathy" or "retinopathy associated with diabetes mellitus" is that disorder caused by increased permeability of the capillaries in the eye which leads to hemorrhages and edema in the eye and can lead to blindness. The term "small vessel disorders associated with diabetes mellitus" includes, but is not limited to, diabetic retinopathy and peripheral vascular disease.

The magnitude of a prophylactic or therapeutic dose of DCL in the acute or chronic management of disease will vary with the severity of the condition to be treated and the route of administration. The dose, and perhaps the dose frequency, will also vary according to the age, body weight, and response of the individual patient. In general, the total daily dose range, for the conditions described herein, is from about 0.1 mg to less than about 10 mg administered in single or divided doses orally, topically, transdermally, or locally by inhalation. For example, a preferred oral daily dose range should be from about 0.1 mg to about 5 mg. A more preferred oral dose is about 0.2 mg to about 1 mg.

It is further recommended that children, patients aged over 65 years, and those with impaired renal or hepatic function initially receive low doses, and that they then be titrated based on individual response(s) or blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response.

The term "therapeutically effective amount of DCL or a pharmaceutically acceptable salt thereof" is encompassed by the above-described dosage amounts. In addition, the terms "said composition comprising (i) a therapeutically effective amount of DCL or a pharmaceutically acceptable salt thereof, and (ii) a therapeutically effective amount of at least one non-steroidal antiinflammatory agent or non-narcotic or a pharmaceutically acceptable salt thereof"; and "said composition comprising (i) a therapeutically effective amount of DCL or a pharmaceutically acceptable salt thereof, and (ii) a therapeutically effective amount of a decongestant such as pseudoephedrine or a pharmaceutically acceptable salt thereof" are also encompassed by the above-described dosage amounts and dose frequency schedule.

Any suitable route of administration may be employed for providing the patient with an effective dosage of DCL according to the methods of the present invention. For example, oral, rectal, parenteral, transdermal, subcutaneous, intramuscular, and like forms of administration may be employed. Dosage forms include tablets, troches, dispersions, suspensions, solutions, capsules, patches, and the like.

The pharmaceutical compositions used in the methods of the present invention comprise DCL, the metabolic derivative of loratadine, as active ingredient, or a pharmaceutically acceptable salt thereof, and may also contain a pharmaceutically acceptable carrier, and optionally, other therapeutic ingredients.

The term "pharmaceutically acceptable salt" refers to a salt prepared from pharmaceutically acceptable non-toxic acids or bases including inorganic acids or bases or organic acids or bases. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases include metallic salts made from aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylglucamine), lysine and procaine.

The compositions for use in the methods of the present invention include compositions such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets), with the oral solid preparations being preferred over the oral liquid preparations. The most preferred oral solid preparations are tablets.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compound for use in the methods of the present invention may also be administered by controlled release means and/or delivery devices such as those described in U.S. Pat. Nos. 3,845,770; 3,916,899; 3,536,809; 3,598,123; and 4,008,719, the disclosures of which are hereby incorporated by reference.

Pharmaceutical compositions for use in the methods of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Desirably, each tablet contains from about 0.1 mg to less than about 10 mg of the active ingredient, and each cachet or capsule contains from about 0.1 mg to about less than 10 mg of the active ingredient, i.e., DCL.

The invention is further defined by reference to the following examples describing in detail the preparation of the compound and the compositions used in the methods of the present invention, as well as their utility. It will be apparent to those skilled in the art that many modifications, both to materials and methods, may be practiced which are within the scope of this invention.

4. EXAMPLES

4.1 Example 1

Preparation of Loratadine and its Metabolites

Loratadine can be synthesized by methods disclosed in U.S. Pat. No. 4,282,233. The metabolites are prepared similarly, by reaction steps conventional in the art, as described in U.S. Pat. No. 4,659,716 which is incorporated here by reference in its entirety. One common method of preparing DCL is to reflux loratadine in the presence of sodium hydroxide and ethanol as depicted below.

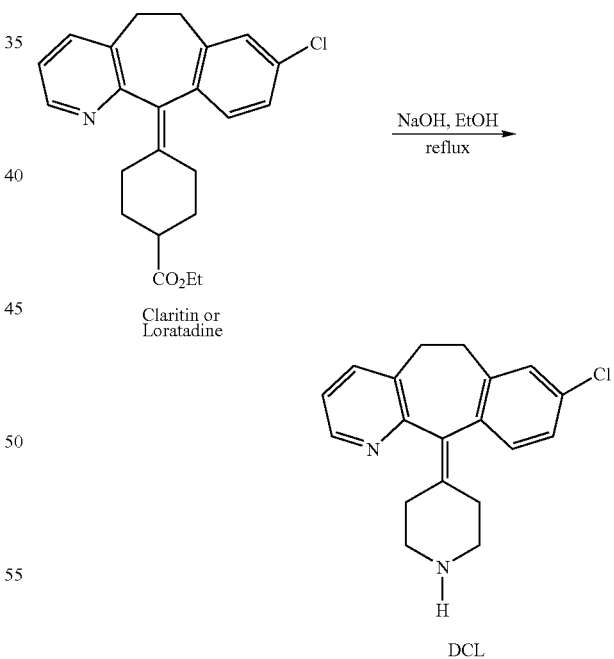

Extraction of Commercially Available Claritin Tablets (600× 10 mg):

Tablets of loratadine, were diluted with water and chloroform. The mixture was stirred, then filtered through celite, rinsed with chloroform until the filtrate contained no loratadine. The separated aqueous layer was extracted with chloroform twice. The combined organic layer was washed with water, brine and dried over sodium sulfate. The solvent was evaporated to give pure loratadine as a white solid.

Saponification of Loratadine:

Loratadine (4.0 g) was added to a solution of sodium hydroxide (5.9 g) in 280 mL of absolute ethanol and the mixture was stirred at reflux for four days. The mixture was cooled and concentrated to remove ethanol. The residue was diluted with water and aqueous layer was extracted with methylene chloride five times. The combined organic layer was washed with water, brine and dried over sodium sulfate. The solvent was evaporated to give 2.82 g (87%) of pure loratadine derivative (or metabolite) as a pale-tan solid.

4.2 Example 2

Antihistaminic Activity

The antihistaminic activity of loratadine and DCL were compared in isolated strips of guinea pig ileum contracted with histamine. This preparation is generally accepted by those skilled in the art as predicative of its efficacy as a peripheral histamine H-1 receptor.

Methods:

Experiments were performed on pieces of ileum taken from male guinea pigs (Hartley strain, 419–560 grams; Elm Hill Breeding Laboratories, Chelmsford, Mass.). The tissues were suspended in tissue chambers containing 40 ml of Tyrode's solution aerated with 95% oxygen and 5% carbon dioxide at 35° C. The Tyrode's solution contained (in mM) 137 NaCl, 2.7 KCl, 2.2 $CaCl_2$, 0.025 $MgCl_2$, 0.4 $NaHPO_4$, 11.9 $NaHCO_3$ and 5.5 glucose. Contractions in response to histamine were recorded with isotonic transducers (Model 357, Harvard Apparatus Company, South Natick, Mass.) using an ink-writing polygraph (Model 7, Grass Instrument Company, Quincy, Mass.). A tension of one gram was maintained on all tissues at all times.

In each experiment three or four pieces of ileum were removed from a single animal, suspended in individual tissue chambers and allowed to equilibrate with the bathing solution for one hour before the administration of any drugs. In four initial experiments in which tissues were exposed to histamine at concentrations of $1 \times 10^{-7}$, $1 \times 10^{-6}$ and $1 \times 10^{-5}$ mol/l, histamine at $1 \times 10^{-6}$ mol/l produced strong contractions on the linear portion of the log-concentration-effect curve and this concentration of histamine was chosen for use in all further experiments.

For determining the antihistaminic effects of loratadine and DCL, tissues were exposed briefly (about 15 seconds) to $1 \times 10^{-6}$ mol/l of histamine at intervals of 15 minutes. After two successive exposures to histamine produced contractions of approximately the same magnitude, loratadine or DCL, at final concentrations that varied three- or ten-fold, was added to all but one of the tissue chambers, the untreated tissue serving as a control for the treated tissues. After each exposure of drug-treated tissues to histamine, the fluid in the tissue chamber was replaced with fluid free of histamine but containing the same drug at the same concentration. The histamine challenges were made at 5, 20, 35, 50, 65, 80, 95, 110 and 125 minutes of exposure to the drug or at comparable times in the control tissues.

Subsequent analyses of the results from each experiment involved (i) normalization of the data from each tissue for differences in inherent contractility by expressing all contractions as a percent of the last predug contraction, (ii) normalization of the data for possible time-related changes in contractility by expressing the contractions recorded during drug-exposure as a percent of the corresponding value for the untreated tissue, and finally (iii) calculation of the drug-related percent reduction of each contraction.

The resultant sets of data for drug concentration and corresponding percent reduction in histamine-response were then used to estimate for each experiment the concentration of drug that would have produced a 50 percent reduction in the histamine response, the $IC_{50}$. This was done by fitting straight lines to the data using the method of least squares and calculating the $IC_{50}$ from the equation of the line. The mean +/− standard error of the values for the experiments on each drug were calculated, and differences between the drugs was examined using the Kruskal Wallis 1-way analysis of variance by ranks.

A summary of the results are shown in the following two tables. The percentages of reduction of histamine-induced contractions of the isolated guinea pig ileum produced by exposure for 125 minutes to various concentrations of each drug are set forth below:

TABLE 1

Reduction of Histamine-induced Guinea Pig Ileum Contractions (Percent)

| Drug | Expt No. | Concentration of drug (mol/l) | | | | | |
|---|---|---|---|---|---|---|---|
| | | $3 \times 10^{-10}$ | $1 \times 10^{-9}$ | $3 \times 10^{-9}$ | $1 \times 10^{-8}$ | $3 \times 10^{-8}$ | $1 \times 10^{-7}$ |
| Loratadine | 1 | — | 19.05 | — | 13.33 | — | 88.57 |
| | 2 | — | — | — | 28.32 | 54.42 | 98.66 |
| | 3 | — | — | — | 39.64 | 44.68 | 93.38 |
| | 4 | — | — | — | 55.86 | 45.83 | 86.46 |
| DCL | 1 | 11.93 | 73.12 | | | | |
| | 2 | 38.91 | 38.81 | 56.71 | | | |
| | 3 | 40.00 | 62.69 | 76.21 | | | |
| | 4 | 35.43 | 44.13 | 76.43 | | | |

TABLE 2

Reduction of Histamine-induced Guinea Pig Icum Contractions ($IC_{50}$)

| Drug | Expt | $IC_{50}$(M) |
|---|---|---|
| Loratadine | 1 | $1.90 \times 10^{-8}$ |
| | 2 | $2.21 \times 10^{-8}$ |
| | 3 | $2.10 \times 10^{-8}$ |
| | 4 | $1.22 \times 10^{-8}$ |

TABLE 2-continued

Reduction of Histamine-induced
Guinea Pig Icum Contractions (IC$_{50}$)

| Drug | Expt | IC$_{50}$(M) |
|---|---|---|
| | Mean | $1.86 \times 10^{-8}$ |
| | S.E. | 0.22 |
| DCL | 1 | $6.36 \times 10^{-10}$ |
| | 2 | $19.2 \times 10^{-10}$ |
| | 3 | $5.26 \times 10^{-10}$ |
| | 4 | $8.66 \times 10^{-10}$ |
| | Mean | $9.75 \times 10^{-10}$ |
| | S.E. | 3.20 |

Note: There is a statistically significant drug-related difference in IC$_{50}$ values (P = 0.0209).

These results indicate that DCL is approximately 20 fold more potent at the histamine receptor than loratadine.

4.3 Example 3

Receptor Binding Studies

Receptor binding studies on the binding affinities of loratadine and DCL at histamine H-1 receptors were performed.

The methods described by Dini et al., which is hereby incorporated by reference herein (Agents and Actions, 33:181–184, 1991), were used for these binding studies. Guinea pig cerebella membranes were incubated with 0.5 nM 3H-pyrilamine for 10 min at 25° C. Following incubation, the assays were rapidly filtered under vacuum through GF/B glass fiber filters (Whatman) and washed several times with ice-cold buffer using a Brandel Cell Harvester. Bound radioactivity was determined with a liquid scintillation counter (LS 6000, Beckman) using a liquid scintillation cocktail (Formula 989, DuPont NEN).

IC$_{50}$ values were determined for compounds tested and pyrilamine at the H-1 histamine receptor:

TABLE 3

Inhibition of Pyrilamine Binding at H-1 Receptor

| | H-1 receptor | |
|---|---|---|
| Compound | IC$_{50}$(nM) | (nH) |
| Loratadine | 721 | (1.55) |
| DCL | 51.1 | (1.12) |
| Pyrilamine | 1.4 | (0.98) |

As shown above, DCL was found to have a 14 fold greater affinity than loratadine for histamine H-1 receptors. These results are consistent with the findings demonstrating a higher potency of DCL over loratadine for inhibition of histamine-induced contractions of guinea pig ileum.

These studies confirm that DCL has a higher potency for histamine receptors than loratadine.

4.4 Example 4

Tumor Promoting Activity

Inhibition of lymphocyte mitogenesis was used to screen the potencies of loratadine and DCL as tumor promoting agents.

Mitogenesis Studies:

Fresh spleen cells ($5 \times 10^5$) obtained from 5-week old BALB/c mice (Charles River, ST. Constant, PQ) were suspended in RPMI 1640 medium containing 2% fetal calf serum (Grand Island Biological Co., Grand Island, N.Y.) seeded into replicate microwell plates (Nunc) to which concanavalin (Con) A (2 µg/ml; Sigma Chemical Co., St. Louis, Mo.) was added and incubated (37° C., 95% air, 5% CO$_2$) in the absence or presence of increasing concentrations of the test agents dissolved in saline or other vehicles. Forty-three hours after the addition of Con A, 0.25 nmol $^3$H-thymidine (6.7 Ci/nmol; ICN Radiopharmaceuticals, Montreal, PQ) was added to each well. After an additional 5-hour incubation, the cells were washed from the wells onto filter papers employing an automated cell sorter. The filters were placed into vials containing 5 ml scintillation fluid (Readysafe; Beckman), and radioactivity incorporated into DNA at 48 hours was determined (n=3). IC$_{50}$ values for inhibition of mitogenesis were determined over wide range of concentrations (0.1 to 10 µM).

TABLE 4

Inhibition of Concanavalin A
Induced Stimulation of Lymphocytes (IC$_{50}$)

| Loratadine | 1.0 µM |
|---|---|
| DCL | 5.6 µM |

These results indicate that DCL is 5-7 fold less active than loratadine at promoting tumor growth.

4.5 Example 5

Cardiovascular Effects

The effects of DCL on cardiac potassium currents were studied.

Methods:

Single ventricular myocytes of the guinea-pig and the rabbit were dissociated by enzymatic dispersion (see Carmeliet, *J. Pharmacol. Exper. Ther.*, 1992, 262, 809–817 which is incorporated herein by reference in its entirety). The single suction patch electrode, with a resistance of 2 to 5 MΩ was used for voltage clamp (Axoclamp 200A). P-clamp software (Axon Instruments) was used to generate voltage-clamp protocols and to record and analyze data. The standard solution contained in mM: NaCl 137.6, KCl 5.4, CaCl$_2$ 1.8, MgCl$_2$ 0.5, HEPES 11.6 and glucose 5, and NaOH was added to pH 7.4. The intracellular solution contained KCl 120, MgCl$_2$ 6, CaCl$_2$ 0.154, Na$_2$ATP 5, EGTA 5, and HEPES 10, with KOH added until pH 7.2.

Effect on the Delayed Rectifying K$^+$ Current, (I$_{kr}$) in Rabbit Ventricular Myocytes:

The voltage clamp protocol consisted of clamps from a holding potential of −50 mV to +10 mV for a duration of 4 sec. The change in tail current was measured as a function of the drug concentration. This concentration was changed between $10^{-7}$ and $10^{-5}$ M in five steps. Exposure to each concentration lasted 15 min. At the end, washout was attempted during 30 min.

Effect on the Inward Rectifier Current in Guinea-Pig Myocytes:

The inward rectifier was measured by applying ramp voltage clamps starting from −50 mV and hyperpolarizing the membrane to −120 mV at a speed of 10 mV/sec. The starting concentration was the 50% efficiency concentration, determined in the preceding experiments. Higher concentrations were applied if this initial concentration was without effect.

Effect on $IK_s$ in Guinea-Pig Ventricular Myocytes:

Tail currents were measured following depolarizing clamps of 2 sec duration to potentials between −30 mV and +60 mV; holding potential −50 mV.

The results from these studies indicate that DCL is less active than terfenadine in inhibiting the cardiac delayed rectifier and thus has no potential for cardiac side-effects. Thus, the methods of the present invention are less toxic than methods which use other non-sedating antihistamines.

4.6 Example 6

Inhibition of Cytochrome P450

This study is conducted to determine the extent that loratadine and DCL inhibit human cytochrome P4503A4 (CYP3A4). CYP3A4 is involved in many drug—drug interactions and quantitation of inhibition of CYP3A4 by loratadine or DCL indicates the potential of such drug—drug interactions. Inhibition is measured using the model substrate testosterone and cDNA-derived CYP3A4 in microsomes prepared from a human lymphoblastoid cell line designated h3A4v3.

Study Design:

The inhibition study consists of the determination of the 50% inhibitory concentration ($IC_{50}$) for the test substance. A single testosterone concentration (120 μM, approximately twice the apparent Km) and ten test substance concentrations, separated by approximately ½ log, are tested in duplicate. Testosterone metabolism is assayed by the production of the 6(β)-hydroxytestosterone metabolite. This metabolite is readily quantitated via HPLC separation with absorbance detection.

Storage/Preparation of the Test Substances and Addition to the Incubations:

The test substances will be stored at room temperature. The test substances will be dissolved in ethanol for addition to the incubations. The solvent concentration will be constant for all concentrations of the test substance.

$IC_{50}$ Determination:

Final test substance concentrations will be 100, 30, 10, 3, 1, 0.3, 0.1, 0.03, 0.01, 0.003 and 0 μM. Each test concentration will be tested in duplicate incubations in accordance with the method below:

Method:

A 0.5 ml reaction mixture containing 0.7 mg/ml protein, 1.3 mM NADP+, 3.3 mM glucose-6-phosphate, 0.4 U/ml glucose-6-phosphate dehydrogenase, 3.3 mM magnesium chloride and 120 μM testosterone in 100 mM potassium phosphate (pH 7.4) will be incubated at 37° C. for 30 min. A known quantity of 11(β)-hydroxytestosterone will be added as an internal standard to correct for recovery during extraction. The reaction mixture will be extracted with 1 ml methylene chloride. The extract will be dried over anhydrous magnesium sulfate and evaporated under vacuum. The sample will be dissolved in methanol and injected into a 4.6×250 mm 5u C18 HPLC column and separated at 50° C. with a mobile phase methanol/water at a flow rate of 1 ml per min. The retention times are approximately 6 min for the 6(β)-hydroxy, 8 min for 11(~)-hydroxy and 12 min for testosterone. The product and internal standard are detected by their absorbance at 254 nm and quantitated by correcting for the extraction efficiency using the absorbance of the 11(β)-hydroxy peak and comparing to the absorbance of a standard curve for 6(β)-hydroxytestosterone.

Data Reporting:

For each test substance, the concentration of 6(β)-hydroxytestosterone metabolite in each replicate incubation is determined and the percentage inhibition relative to solvent control is calculated. The $IC_{50}$ is calculated by linear interpolation.

Useful pharmaceutical dosage forms for administration of the compounds used in the methods of the present invention can be illustrated as follows:

4.7. Example 7

Capsules

A large number of unit capsules are prepared by filling standard two-piece hard gelatin capsules each with 0.1 to 10 milligrams of powdered active ingredient, 150 milligrams of lactose, 50 milligrams of cellulose, and 6 milligrams magnesium stearate.

4.8. Example 8

Soft Gelatin Capsules

A mixture of active ingredient in a digestible oil such as soybean oil, lecithin, cottonseed oil or olive oil is prepared and injected by means of a positive displacement pump into gelatin to form soft gelatin capsules containing 0.1 to 10 milligrams of the active ingredient. The capsules are washed and dried.

4.9 Example 9

Tablets

A large number of tablets are prepared by conventional procedures so that the dosage unit was 0.1 to 10 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited patents or publications may provide further useful information these cited materials are hereby incorporated by reference in their entireties.

What is claimed is:

1. A method of treating urticaria in a human comprising orally administering to a human a therapeutically effective amount of descarboethoxyloratadine (DCL) or a pharmaceutically acceptable salt thereof, wherein the therapeutically effective amount is from 0.1 to 5.0 mg per day.

2. The method of claim 1 wherein the amount of said descarboethoxyloratadine (DCL) is administered together with a pharmaceutically acceptable carrier.

* * * * *